United States Patent [19]

Stein et al.

[11] 4,064,142
[45] Dec. 20, 1977

[54] α-TRICHLOROMETHYL THENYL PHENYLETHERS AND SULFIDES

[75] Inventors: Robert George Stein, Kenosha, Wis.; Terry Lee Couch, Waukegan; Aldo Joseph Crovetti, Lake Forest, both of Ill.

[73] Assignee: Abbott Laboratories, North Chicago, Ill.

[21] Appl. No.: 720,187

[22] Filed: Sept. 3, 1976

Related U.S. Application Data

[62] Division of Ser. No. 565,996, April 7, 1975.

[51] Int. Cl.² .............. C07D 333/16; C07D 333/12; A01N 9/00
[52] U.S. Cl. .................. 260/332.3 R; 260/329 S; 260/332.5; 424/275
[58] Field of Search ............. 260/332.5, 332.3 P, 260/332.3 R, 329 S

[56] References Cited

U.S. PATENT DOCUMENTS 2,329,074  9/1943  Muller .................. 260/332.5

Primary Examiner—James O. Thomas, Jr.
Assistant Examiner—A. Siegel
Attorney, Agent, or Firm—Paul D. Burgauer; Robert L. Niblack

[57] ABSTRACT

Biodegradable insecticides having the formula:

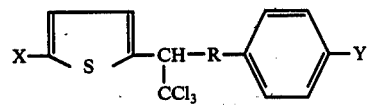

where X, Y and R are different, and X and Y are selected from the group consisting of hydrogen, halo, lower alkyl and lower alkoxy, and R is selected from the group consisting of nitrogen, oxygen, sulfur and sulfone.

3 Claims, No Drawings

α-TRICHLOROMETHYL THENYL PHENYLETHERS AND SULFIDES

This is a division of application Ser. No. 565,996 filed Apr. 7, 1975.

SUMMARY OF THE INVENTION

The present invention relates to novel thenyl derivatives and to methods for their preparation. The compounds of this invention are useful as biodegradable insecticides and molluscides.

The trichloromethyl thenyls of the present invention are improved insecticides and molluscides which are biodegradable and exhibit low mammalian toxicity. Such compounds are represented by the formula

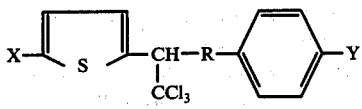

where X and Y are selected from the group of hydrogen, halo, lower alkyl and lower alkoxy; and R is selected from the group of oxygen, sulfur and sulfone.

As used herein, the term "halo" means halogens, as illustrated by, but not limited to chlorine, bromine, iodine and fluorine.

As used herein, the term "lower alkoxy" means oxygenous straight and branched chain radicals of from 1 to 8 carbon atoms, as illustrated by, but not limited to methoxy, ethoxy, and the like.

As used herein, the term "lower alkyl" means straight and branched chain radicals of from 1 to 8 carbon atoms, as illustrated by, but not limited to methyl, ethyl, butyl and the like.

BACKGROUND OF THE INVENTION

Many mollusks including snails and slugs, terrestrial as well as aquatic cause serious economic and health problems in many parts of the world. Snails which are members of a large class of gastropod mollusks including most forms having a univalve shell or having no shell can be quite injurious to vegetation as they destroy many varieties of beneficial agricultural plants. Even more harmful is the role that they play in the life cycle of many tropical and semitropical diseases. Millions of people and countless animals in many parts of the world are afflicted with these diseases. Snails play a significant role in the growth cycle of the parasite involved in these diseases. In the snails the parasite larval stages develop and emerge to enter warm-blooded animals and mature into worms. The worms in turn lay eggs which are carried to vital organs in the animal or human body by the bloodstream. Lastly, the eggs find their way back to the snails through water supplies and the like and the cycle begins once again. Thus, a single snail can be the ancestor of many millions of new snails per year.

For example, snails of the genre Oncomelania, Australorbis and Bulinus are schistosome intermediate hosts. Likewise, snails of the genre Lymnaca are intermediate hosts for the liver fluke worm. Snails of these genre particularly cause debilitating human problems. Specifically, bilharziasis has long been endemic in various parts of the world, and is even on the increase.

While various controls methods of bilharziasis and other diseases of this type have been suggested, the destruction of intermediate snail hosts by toxic chemicals appears to be the most rapid and effective means for reducing transmission of many tropical and semitropical diseases.

However, many chemicals useful in combating mollusks such as snails, such chemicals generically termed as molluscicides, have certain disadvantages. In some cases they are difficult to formulate and in certain types of habitats available formulations do not disperse effectively. In other instances the chemical itself is irritating and potentially dangerous to the handler, is required for use at relatively high dosages, and may be prematurely used up by absorption by soil and organic material. Again, other molluscicides on the market are ineffective at a high pH, are corrosive to equipment or their activity is reduced by bright sunlight. Lastly, some molluscicides while sufficiently active are inactivated at a low pH and/or do not kill snail eggs.

DDT[1,1,1,-trichloro-2-bis(p-chlorophenyl) ethane] has been widely used as an insecticide. However, its usefulness has diminished because of environmental hazards and a low degree of biodegradability.

Thus, continued use of DDT poses an environmental dilemma. Insecticides are required to control vector born diseases and to help protect the food supplies of the world. However, the micropollutants liberated into the environment by DDT threatens both the environment and the existence of many different animals. There is therefore, an urgent need to develop persistent, biodegradable insecticides that would act very much like DDT, but yet, would be rapidly biodegradable and then excreted.

DDT acts as an inducer of microsommal oxidase enzymes in the vertibrate liver. The injurious nature of DDT arises because of the stability of the aryl-chlorine bond, which is not attacked to any extent by the multifunction oxidase enzyme of living tissue. Therefore, compounds like DDT are stored in lipid tissues, instead of being metabolized and eliminated from the body. To produce biodegradable analogs, it is necessary to provide sites for attack by multifunctional oxidases.

It has been shown that by attaching "handles" to the DDT molecule, it is possible to obtain biodegradability. (Metcalf-*Chemtech*, Feb. 1972; 105) This biodegradability is produced by the fact that the multifunctional oxidases will attack the "handle", and thus, cause side chain oxidation to less lipid solubile molecules. As a result of these handles, biodegradability is obtained, and thus there is a much less toxic effect than with DDT. With these handles the multifunction oxidases, convert the lipid partitioning substrates of DDT into more water soluble molecules that are excreted from animal bodies, rather than being stored in fatty tissues and concentrated through ecological magnification.

DESCRIPTION OF THE INVENTION

The present invention provides compositions which are effective and persistent insecticides and molluscides in inanimate situations. Yet when such compositions are absorbed into living organisms, they contain one or more points readily susceptible for attack by the MFO enzymes, thus promoting rapid detoxification of the insecticides and molluscides. Such compositions are readily biodegradable, relatively stable and inexpensive. These compositions are "DDT Type", and have "handles" which are acted upon by the MFO enzymes and thereby are biodegradable or metabolicly converted into environmentally accepted products. These compositions also contain an additional route which contributes to its insecticidal activity and/or the relatively low mammalian toxicity exhibited by the compositions of the invention.

It has been found that asymmetrical DDT analogs having the following formula,

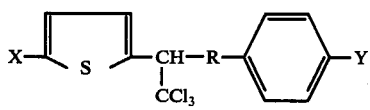

where X, Y, and R are different, and X and Y are selected from the group of halo, lower alkyl, and lower alkoxy; and R is selected from the group of nitrogen, oxygen, sulphur and sulfone.

The inventive compounds were then screened for their insecticide and molluscide activity. Table II below outlines results obtained with regard to particular compounds.

TEST 1

Two-spotted Spider Mites Screen — Spray Method. *Tetranychus urticae*

PROCEDURE: One Henderson Bush Lima Bean Plant, 8–10 days old, with a 24 hr. infestation of mites is used for each dilution of the chemical tested. Chemicals are initially screened at 2500 ppm. A stock solution of 50,000 ppm, made in 25 percent DMF and 75 percent IPA with 4 percent Tween 20 is diluted to 2500 ppm (1:20) in a diluent consisting of 50 percent acetone and 50 percent $H_2O$ with 0.1 percent Tween 20 per 100 ml.

Using a deVilbus like atomized spray, the top and underside of both leaves are sprayed with approximately 5 ml. of the appropriate dilution. A fine mist must cover both sides of the leaf. Mortality is noted after 48 hours.

EVALUATION: Using a dissecting scope, both sides of the leaf are examined. Candidates rated 3 are rescreened at 2500 ppm. If rated 3 a second time, they are further tested at levels of 2500 ppm, 250 ppm, 100 ppm, 25 ppm.

80 – 100 percent mortality = 3
50 – 80 percent mortality = 2
25 – 50 percent mortality = 1
< 25 percent mortality = 0

TEST II

House Fly — *Musca domestica* — *Linnacus*

PROCEDURE: Approximately 50 three day old adult houseflies are used for each dilution of the chemical tested. Chemicals are initially screened at 2500 ppm. A stock solution of 50,000 ppm made in 25 percent DMF and 75 percent IPA with 4 percent Tween 20 is diluted to 2500 ppm (1:20) using 70 percent acetone - $H_2O$ as diluent.

Flies are anesthetized with $CO_2$ and placed in a Buchner funnel. The appropriate dilution is poured onto the flies. Contact time is approximately 5 seconds. The chemical is removed by suction and the flies are then transferred to pint ice-cream containers. These are covered with saran wrap and mortality noted after 1 hour.

EVALUATION: The candidates rated 3 are rescreened at 2500 ppm and if activity persists, they are further tested at 2500 ppm, 250 ppm, 100 ppm, 25 ppm, 10 ppm and 1.0 ppm to determine minimum lethal dose.

80 – 100 percent mortality = 3 or marked activity
50 – 80 percent mortality = 2 or moderate activity
25 – 50 percent mortality = 1 or slight activity
25 percent mortality = 0 or inactive

TEST III

Cabbage Looper, *Trichoplusia ni*

PROCEDURE: Approximately 15 day old cabbage looper larvae are used for each dilution of the chemical tested. Chemicals are initially screened at 2500 ppm. A stock solution of 50,000 ppm made in 25 percent DMF and 75 percent IPA with 4 percent Tween 20, is diluted to 2500 ppm (1:20) in a diluent of 70 percent acetone and $H_2O$.

The larvae are placed in a Buchner funnel. The appropriate dilution is poured onto them. Contact time is approximately 5 seconds. The chemical is removed by suction and the worms are placed in a petri dish along with a leaf from a Henderson Bush Lima Bean Plant. 24 hours later mortality is determined.

EVALUATION: A candidate rated 3 is rescreened at 2500 ppm. If again rated 3 the compound is retested at 2500 ppm, 250 ppm, 100 ppm, 25 ppm, 10 ppm, 1.0 ppm to determine minimum lethal dose. Rating schedule:

80 – 100 percent mortality = 3 marked activity
50 – 80 percent mortality = 2 moderate activity
25 – 50 percent mortality = 1 slight activity
25 percent mortality = 0 Inactive

TEST IV

Molluscide Screening Test

Newly hatched snails of the strain B. glabrata numbering 20 were placed in well water at a temperature of 26° C. Test chemical was added to the well water in an amount to provide 10 ppm. After 24 hours exposure to the chemicals the newly hatched snails were then examined for mortality rates.

The general mode of synthesis illustrating the methods used to obtain the compounds of this group are attached below.

General Mode of synthesis

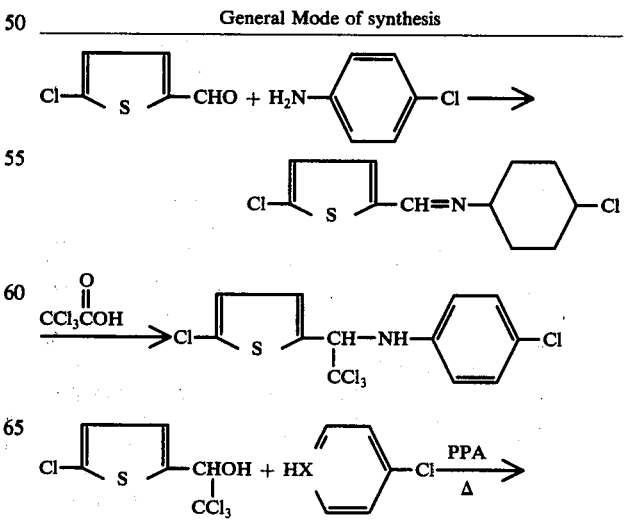

-continued
General Mode of synthesis

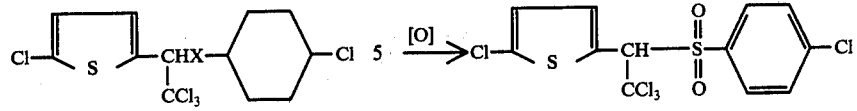

X = O and/or S

The attached Tables illustrate the characteristics and results of particular compounds.

Table I (Schiff Bases) Intermediates
*T/F

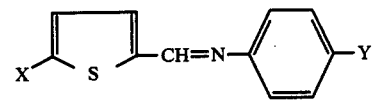

| NO. | X | Y | MP | C | H | N |
|---|---|---|---|---|---|---|
| 1 | H | Cl | 72–73 | 59.59 | 3.63 | 6.31 |
|   |   |   |       | 59.90 | 3.63 | 6.43 |
| 2 | Cl | Cl | 84–85 | 51.58 | 2.75 | 5.46 |
|   |    |    |       | 51.89 | 2.79 | 5.55 |
| 3 | Cl | CH₃ | 72–73 | 61.14 | 4.27 | 5.93 |
|   |    |     |       | 61.50 | 4.28 | 6.38 |
| 4 | Cl | OCH₃ | 96–97 | 57.34 | 4.07 | 5.65 |
|   |    |      |       | 57.26 | 4.00 | 5.56 |
| 5 | Cl | OC₂H₅ | 94–95 | 58.75 | 4.54 | 5.26 |
|   |    |       |       | 58.79 | 4.59 | 5.36 |
| 6 | Cl | F | 59–60 | 55.12 | 2.94 | 5.84 |
|   |    |   |       | 55.28 | 2.90 | 5.94 |
| 7 | CH₃ | Cl | 101–102 | 61.14 | 4.27 | 5.93 |
|   |     |    |         | 61.36 | 4.36 | 6.20 |
| 8 | CH₃ | CH₃ | 83–84 | 72.54 | 6.09 | 6.51 |
|   |     |     |       | 72.77 | 6.12 | 4.47 |
| 9 | CH₃ | OC₂H₅ | 95–96 | 68.55 | 6.26 | 5.71 |
|   |     |       |       | 68.05 | 6.25 | 5.71 |

All compounds recrystallized from Cyclohexane
*Theory/Found

TABLE II

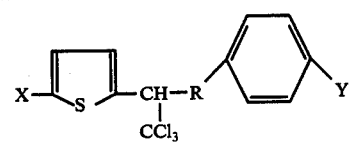

| | | | | MP Recrystal- lization Solvent | T/F C | H | N | Insecticide Mites 2500 ppm | Fly 2500 ppm | Looper 2500 ppm | Molluscide Mortality Adult 10 ppm | 1 ppm | New 10 ppm | 1 ppm |
|---|---|---|---|---|---|---|---|---|---|---|---|---|---|---|
| No. | X | Y | R | | | | | | | | | | | |
| 1 | H | Cl | NH | 73–74 EtOH | 42.25 42.18 | 2.65 2.66 | 4.10 4.17 | 0 | 1 | 1 | 0/10 | 0/10 | 6/10 | 0/10 |
| 2 | Cl | Cl | NH | 122–123 Cyclohexane | 38.38 38.96 | 2.14 2.25 | 3.72 3.86 | 2 | 2 | 3 | 7/10 | 0/10 | 10/10 | 5/10 |
| 3 | Cl | CH₃ | NH | 118–119 Cyclohexane | 43.97 44.33 | 3.12 3.22 | 3.94 4.10 | 2 | 2 | 0 | 4/10 | 0/10 | 10/10 | 6/10 |
| 4 | Cl | OCH₃ | NH | 46–47 Pentane | 42.07 42.26 | 2.98 3.08 | 3.77 3.86 | 1 | 1 | 0 | 3/10 | 0/10 | 8/10 | 4/10 |
| 5 | Cl | OC₂H₅ | NH | 53–54 EtOH | 43.77 43.91 | 3.14 3.41 | 3.64 3.70 | 2 | 2 | 2 | 3/10 | 0/10 | 10/10 | 4/10 |
| 6 | Cl | F | NH | 73–74 Cyclohexane | 40.14 40.20 | 2.24 2.20 | 3.89 3.95 | 3 | 0 | 1 | 10/10 | 0/10 | 10/10 | 4/10 |
| 7 | CH₃ | Cl | NH | Oil | 43.97 44.05 | 3.12 3.26 | 3.94 3.88 | 0 | 2 | 1 | 6/10 | 0/10 | 10/10 | 2/10 |
| 8 | CH₃ | CH₃ | NH | 53–54 Pentane | 50.24 50.19 | 4.21 4.22 | 4.18 4.24 | 0 | 2 | 0 | 10/10 | 2/10 | 10/10 | 3/10 |
| 9 | CH₃ | OC₂H₅ | NH | 63–64 EtOH | 49.40 49.37 | 4.42 4.47 | 3.83 4.01 | 0 | 2 | 2 | 6/10 | 1/10 | 10/10 | 4/10 |
| 10 | Cl | Cl | O | 79–80 Pentane | 38.28 38.50 | 1.87 1.94 | | 2 | 0 | 1 | 4/10 | 1/10 | 10/10 | 6/10 |
| 11 | Cl | CH₃ | O | 99–101 Pentane | 43.84 44.05 | 2.83 2.87 | | 0 | 0 | 0 | | | | |
| 12 | Cl | Cl | S | 57–58 EtOH | 36.71 37.04 | 1.79 1.73 | | 0 | 0 | 0 | | | | |
| 13 | Cl | Cl | SO₂ | 133–134 EtOH | 33.94 34.50 | 1.66 1.55 | | 0 | 1 | 1 | | | | |
| 14 | Cl | Br | S | Oil | 32.98 | 1.61 | | 3 | 1 | 0 | | | | |

TABLE II-continued

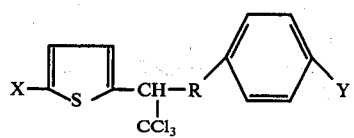

| No. | X | Y | R | MP Recrystallization Solvent | T/F C | H | N | Insecticide Mites 2500 ppm | Fly 2500 ppm | Looper 2500 ppm | Molluscide Mortality Adult 10 ppm | 1 ppm | New 10 ppm | 1 ppm |
|---|---|---|---|---|---|---|---|---|---|---|---|---|---|---|
| | | | | | 33.40 | 1.81 | | | | | | | | |

0-NA (0-25%) % Mortality
1-Slight (25-80%)
2-Moderate (50-80%)
3-Marked (80-100%)

The following examples will serve to illustrate the preparation of the novel α-trichloromethyl thenyl anilines, phenylether, sulfide and sulfones used as biodegradable insecticides and molluscides.

EXAMPLE 1

5-Chloro-2-Thenylidene-4'-chloroaniline and other Schiff Bases found in Table 1

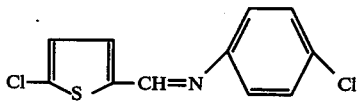

A solution of 43.8 g. (0.30 m.) 5-chloro-2-thiophenecarboxaldehyde, 25.5 g. (0.30 m) p-chloroaniline, 0.5 g. p-toluenesulfonic and 400 ml. benzene was refluxed 6 hours over a Dean-Stark trap to collect water formed. The reaction solution was cooled, washed with dilute sodium carbonate solution and then concentrated in vacuo to a yellow solid. One recrystallization from cyclohexane gave 49 g. of solid melting at 84°-85° C.

Analysis for $C_{11}H_7Cl_2NC$: C, 51.58; H, 2.75; N, 5.46. Found: C, 51.89; H, 2.76; N, 5.55.

EXAMPLE 2

2-(α-Trichloromethyl-5-Chlorothenyl)-4'-Chlorophenylaniline

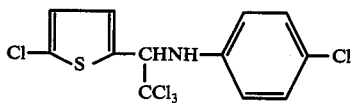

A solution of 25.6 g. (0.10 m.) 5-chloro-2-thenylidene-4'-chloroaniline, 16.4 g. (0.10 m.) trichloroacetic acid and 200 ml. toluene was refluxed for 4 hours. The solution was cooled, washed with 2N hydrochloric acid solution followed by cold water. The solution was treated with decolorizing carbon and concentrated in vacuo. The tan solid was recrystallized from cyclohexane and melted at 122°-123° C.

Analysis for $C_{12}H_8Cl_5N_5$: C, 38.38; H, 2.14; N, 3.72. Found: C, 38.96; H, 2.25; N, 3.86.

EXAMPLE 3

2-(α-Trichloromethyl-5-chlorothenyl)-4'-chlorophenyl ether

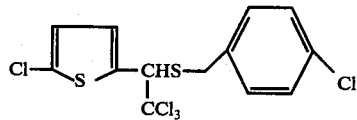

A solution of 10.6 g. (0.04 m.) 2,2,2-trichloro-1-(5-chlorothiophene-2)-ethanol, 5.12 g. (0.04 m.) p-chlorophenol, 36 g. phosphorous pentoxide and 25 ml. 85% phosphoric acid was stirred in an oil bath at 90°-95° C. for 2 hours. The reaction was cooled and carefully poured into ice-water. The mixture was extracted several times with ether. The combined ether washes were washed with cold 5% potassium hydroxide solution followed by water. The ether solution was dried over sodium sulfate, filtered and concentrated to a solid. Several recrystallizations from Skelly B gave analytical pure material melting at 79°-80° C.

Analysis for $C_{12}H_7Cl_5OS$: C, 38.28; H, 1.87. Found: C, 38.50; H, 1.94.

EXAMPLE 4

2-(Trichloromethyl-5-Chlorothenyl)-4'-Chlorophenylthioether

A solution of 57 g. (0.21 m.) 2,2,2 trichloro-1-(5-chlorothiophene-2)-ethanol, 30.3 g. (0.21 m.) p-chlorothiophenol, and 100 ml. of polyphosphoric acid was heated in an oil bath at 110°-120° C. for 16 hours. The solution was cooled and carefully poured into ice-water. The mixture was extracted with ether several times. The combined extracts were washed with dilute sodium hydroxide solution followed by water.

The ethereal solution was dried over magnesium sulfate, filtered and concentrated in vacuo to a tan solid. Several recrystallizations from ethanol gave a tan solid melting at 57°-58° C.

Analysis for $C_{12}H_7Cl_5S_2$: C, 36.71, H, 1.79. Found: C, 37.04; H, 1.73.

EXAMPLE 5

2-(αTrichloromethyl-5-Chlorothenyl)-4'-Chlorophenyl sulfone

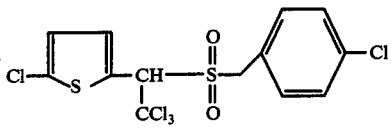

To a solution of 7.84 g. (0.02 m.) 2-( -trichloromethyl-5-chlorothenyl)-4'-chlorophenyl sulfide in 80 ml. glacial acetic acid cooled in an ice-bath at 0°–5° C. was added 10 ml. of 30% hydrogen peroxide. The solution was stirred at ice-bath temperature for 1 hour and at room temperature for 48 hours. The mixture was cooled and then filtered. One crystallization from ethanol gave a white solid melting at 133°–134° C.

Analysis for $C_{12}H_7Cl_5OS_2$: C, 33.94; H, 34.50. Found: C, 34.50; H, 1.55.

Advantageously, the particular new active compounds according to the present invention have strong insecticidal and acaricidal effects as well as molluscidal activity and only a low toxicity towards warm-blooded animals and plants. The effects appear rapidly and are long-lasting. Surprisingly, the instant active compounds have superior activity with respect to insecticidal, molluscidal and acaricidal activity, and can therefore be used with good results for combating noxious sucking and biting insects, Diptera and mites (Acarino), and the like.

The sucking insects contemplated essentially include aphids, such as the peach aphid (*Myzus persicae*), the black bean aphid (*Doralis fabae*); Coccidae, such as *Aspidiotus hederae, Lecanium hesperidum, Pseudococcus martinimus*; Thysanoptera such as *Hercinothrips femoralis*; and bugs, such as the beet bug (*Piesma quadrata*) and the bed bug (*Cimex lectularious*); and the like.

The biting insects contemplated essentially include butterfly larvae, such as *PluteHa maculipennis, Lymantria dispar*; beetles, such as grain weevils (*Sitophilus granarius*), the Colorado beetle (*Leptinotarsa decemlineata*), but also species living in the soil, such as wire worms (*Agriotes sp.*) and cockchafer larvae (*Melolontha melolontha*); cockroaches, such as the German cockroach (*Blatella germanica*); Orthopetera, such as the cricket (*Gryllus domesticus*); termites, such as Reticulitermes; Hymenoptera, such as ants; and the like.

The Diptera contemplated particularly comprise the flies, such as the common fruit fly (*Drosophila melanogaster*), the Mediterranean fruit fly (*Ceratitis capitata*), the house fly (*Musca domestica*) and gnats, such as the mosquito (*Aedes aegypti*); and the like.

The following mites are of particular importance herein: the spider mites (Tetranychidac), such as the common spider mite (*Tetranychus urticae*), the fruit tree spider mite (*Paratetranyclus pilosus*) gall mites, such as the red currant gall mite (*Eriophyes ribis*), and tarsonemides, such as *Tursonemus pallidus*; and also ticks; and the like.

These molluscicides are not merely specific against certain distinct mollusks, but will be effective against all snails and slugs, and mollusks generally, including, for example, species of Australois, such as *A. quadelupensis*, species of Bulinus, such as *B. truncatus, B. angolensis* and *B. glabratus*, species of Tropicorpus, such as *T. centrimetralis*, species of Limnae, such as *L. natalensis, L. bulimoides*, and *L. auricularia, species of Biophalaria, species of Galba, species of Oncomelania, species of Taphius*, such as *T. glabratus*, species of Helisoma such as *H. trivolvis*, species of Marisa, such as *M. cornuarietis*, species of Pomacea, such as *P. lineata* and *P. glauca*, and species of Ocinebra, such as *O. japonica*.

Significantly, the particular new active compounds of the present invention exhibit an especially good systemic action.

The compositions of the present invention can be formed into any insecticidal and molluscidal formulations using techniques used in the art. Thus, dusts, water, dispersions, emulsions and/or solutions can be formulated by the same methods as DDT insecticides are formulated, provided the carrier solvent is compatable and inert and that it does not react or interfere with the insecticidal and biodegradable characteristics.

While the present invention has been described with reference to illustrative examples, various modifications will be apparent for those skilled in the art, and any such modifications are included within the scope and spirit of this invention as defined by the appended claims.

What is claimed is:

1. A chemical compound of the formula

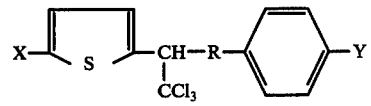

wherein X and Y are selected from the group consisting of hydrogen, halo, lower alkyl and lower alkoxy; and R is oxygen or sulfur.

2. A compound in accord with claim 1, 2-(α-trichloromethyl-5-chlorothenyl)-4'-chlorophenyl ether.

3. A compound in accord with claim 1, 2-(α-trichloromethyl-5-chlorothenyl)-4'-chlorophenyl-thioether.

* * * * *